(12) United States Patent
Biskeborn et al.

(10) Patent No.: US 9,638,614 B2
(45) Date of Patent: May 2, 2017

(54) MEASURING TAPE ABRASIVITY AND WEAR OF A TAPE HEAD-TYPE STRUCTURE

(71) Applicant: International Business Machines Corporation, Armonk, NY (US)

(72) Inventors: Robert G. Biskeborn, Hollister, CA (US); Jason Liang, Campbell, CA (US)

(73) Assignee: International Business Machines Corporation, Armonk, NY (US)

( * ) Notice: Subject to any disclaimer, the term of this patent is extended or adjusted under 35 U.S.C. 154(b) by 420 days.

(21) Appl. No.: 14/105,047

(22) Filed: Dec. 12, 2013

(65) Prior Publication Data

US 2015/0168283 A1 Jun. 18, 2015

(51) Int. Cl.
*G01N 3/56* (2006.01)

(52) U.S. Cl.
CPC ........... *G01N 3/56* (2013.01); *G01N 2203/06* (2013.01)

(58) Field of Classification Search
CPC .............................. G01N 3/56; G01N 2203/06
USPC .................................. 73/7, 8, 86, 87, 861.91
See application file for complete search history.

(56) References Cited

U.S. PATENT DOCUMENTS

| | | | |
|---|---|---|---|
| 3,495,049 A * | 2/1970 | Nelson | G11B 5/00 29/603.09 |
| 3,753,093 A * | 8/1973 | Gardner | G01N 3/56 324/699 |
| 4,091,654 A * | 5/1978 | Hurtig | G01N 3/56 73/7 |
| 5,074,983 A * | 12/1991 | Eltoukhy | C23C 14/0605 204/192.13 |
| 6,040,693 A | 3/2000 | Sakai et al. | |
| 6,118,626 A * | 9/2000 | Muftu | G11B 5/00821 360/122 |

(Continued)

FOREIGN PATENT DOCUMENTS

| | | |
|---|---|---|
| CN | 1643361 A | 7/2005 |
| JP | S62271215 A | 11/1987 |

(Continued)

OTHER PUBLICATIONS

Sourty et al., "Pole Tip Recession in Linear Recording Heads", IEEE Transactions on Magnetics, vol. 39, No. 3, May 2003, pp. 1859-1861.

(Continued)

*Primary Examiner* — Hezron E Williams
*Assistant Examiner* — Marrit Eyassu
(74) *Attorney, Agent, or Firm* — Zilka-Kotab, PC (57) ABSTRACT

Embodiments of the present invention relate to wear measurement. A system according to one embodiment includes a transport mechanism for running a tape across a wear structure and a measuring device for optically measuring an extent of wear of the wear structure. A method according to one embodiment includes positioning a tape across a wear structure, optically determining a first position of a back of the tape relative to a measuring device using the measuring device, running the tape across the wear structure for a period of time, optically determining a second position of the back of the tape relative to the measuring device using the measuring device after the period of time, and determining a difference between the first and second positions.

20 Claims, 8 Drawing Sheets

(56) References Cited

U.S. PATENT DOCUMENTS

| | | |
|---|---|---|
| 6,765,755 B1 | 7/2004 | Jacquet |
| 6,796,884 B1 | 9/2004 | Tran et al. |
| 7,013,705 B2 | 3/2006 | Wortmann et al. |
| 7,161,668 B2 | 1/2007 | Meeks et al. |
| 7,375,327 B2 * | 5/2008 | Yoshiki ............... G01N 23/227 250/305 |
| 7,509,833 B2 | 3/2009 | Biskeborn et al. |
| 7,630,086 B2 | 12/2009 | Oak et al. |
| 7,640,788 B2 | 1/2010 | Biskeborn et al. |
| 7,714,995 B2 | 5/2010 | Meeks |
| 8,621,910 B2 | 1/2014 | Biskeborn et al. |
| 2004/0072033 A1 | 4/2004 | Ide et al. |
| 2004/0115454 A1 | 6/2004 | Lowery et al. |
| 2004/0160604 A1 | 8/2004 | Meeks et al. |
| 2005/0081599 A1 * | 4/2005 | Wortmann ............... G01N 3/56 73/7 |
| 2005/0084621 A1 | 4/2005 | Liu et al. |
| 2005/0284207 A1 * | 12/2005 | Biskeborn ............... G01N 3/56 73/7 |
| 2009/0133468 A1 | 5/2009 | Biskeborn et al. |
| 2010/0269565 A1 * | 10/2010 | Biskeborn ............... G01N 3/56 73/7 |
| 2011/0102944 A1 | 5/2011 | Suzuki |
| 2011/0256423 A1 | 10/2011 | Biskeborn et al. |
| 2013/0186172 A1 | 7/2013 | Biskeborn et al. |
| 2015/0168283 A1 | 6/2015 | Biskeborn et al. |

FOREIGN PATENT DOCUMENTS

| | | |
|---|---|---|
| JP | 10255241 | 9/1998 |
| JP | 2001158895 | 6/2001 |
| JP | 2005285252 | 10/2005 |
| WO | WO03056305 | 7/2003 |

OTHER PUBLICATIONS

Scott et al., "Corrosion and wear studies of uncoated and ultra-thin DLC coated magnetic tape-write heads and magnetic tapes", Wear, vol. 243, 2000, pp. 31-42.

Scott, "Micro/Nanoscale Differential Wear and Corrosion of Multiphase Materials Dissertation", 2001, pp. i-24.

Scott, "Micro/nano-scale differential wear of multiphase materials: pole tip recession in magnetic-tape heads", Wear, vol. 252, 2002, pp. 103-122.

Bhushan et al., "Friction and Wear of Particulate and ME Magnetic Tapes Sliding against a Mn—Zn Ferrite Head in a Linear Mode", IEEE Transactions on Magnetics, vol. 30, No. 6, Nov. 1994, pp. 4176-4178.

Non-Final Office Action from U.S. Appl. No. 13/358,415 dated Mar. 26, 2014.

Ex Parte Quayle from U.S. Appl. No. 13/358,415, dated Jun. 18, 2015.

Notice of Allowance from U.S. Appl. No. 13/358,415, dated Jul. 8, 2015.

Biskeborn et al., U.S. Appl. No. 14/860,535, filed Sep. 21, 2015.

Biskeborn et al., U.S. Appl. No. 14/860,551, filed Sep. 21, 2015.

Restriction Requirement from U.S. Appl. No. 13/358,415, dated Feb. 14, 2014.

Final Office Action from U.S. Appl. No. 13/358,415, dated Oct. 24, 2014.

Final Office Action from U.S. Appl. No. 13/358,415, dated Feb. 25, 2015.

Biskeborn et al., U.S. Appl. No. 13/358,415, filed Jan. 25, 2012.

Biskeborn et al., U.S. Appl. No. 15/409,380, Jan. 18, 2017.

* cited by examiner

MEASURING TAPE ABRASIVITY AND WEAR OF A TAPE HEAD-TYPE STRUCTURE

BACKGROUND

The present invention relates to media abrasivity testing, and more particularly, this invention relates to an improvement in the testing of media abrasivity.

In magnetic storage systems, data is read from and written onto magnetic recording media utilizing magnetic transducers commonly. Data is written on the magnetic recording media by moving a magnetic recording transducer to a position over the media where the data is to be stored. The magnetic recording transducer then generates a magnetic field, which encodes the data into the magnetic media. Data is read from the media by similarly positioning the magnetic read transducer and then sensing the magnetic field of the magnetic media. Read and write operations may be independently synchronized with the movement of the media to ensure that the data can be read from and written to the desired location on the media.

An important and continuing goal in the data storage industry is that of increasing the density of data stored on a medium. For tape storage systems, that goal has led to increasing the track and linear bit density on recording tape, and decreasing the thickness of the magnetic tape medium. However, the development of small footprint, higher performance tape drive systems has created various problems in the design of a tape head assembly, as well as tapes, for use in such systems.

Media abrasivity is directly related to head wear, recession, and spacing loss. Current methods employed by media vendors to gauge abrasivity have been shown to not accurately determine actual head wear, nor tape abrasivity.

BRIEF SUMMARY

A system according to one embodiment includes a transport mechanism for running a tape across a wear structure and a measuring device for optically measuring an extent of wear of the wear structure.

A method according to another embodiment includes positioning a tape across a wear structure, optically determining a first position of a back of the tape relative to a measuring device using the measuring device, running the tape across the wear structure for a period of time, optically determining a second position of the back of the tape relative to the measuring device using the measuring device after the period of time, and determining a difference between the first and second positions.

A method for characterizing a wear stability of a material, according to another embodiment, includes passing a burnished tape across a wear structure, optically determining a first position of a back of the tape relative to a measuring device using the measuring device, running the tape across the wear structure for a period of time, optically determining a second position of the back of the tape relative to the measuring device using the measuring device after the period of time, and determining a difference between the first and second positions.

Other aspects and embodiments of the present invention will become apparent from the following detailed description, which, when taken in conjunction with the drawings, illustrate by way of example the principles of the invention.

DETAILED DESCRIPTION

The following description is made for the purpose of illustrating the general principles of the present invention and is not meant to limit the inventive concepts claimed herein. Further, particular features described herein can be used in combination with other described features in each of the various possible combinations and permutations.

Unless otherwise specifically defined herein, all terms are to be given their broadest possible interpretation including meanings implied from the specification as well as meanings understood by those skilled in the art and/or as defined in dictionaries, treatises, etc.

It must also be noted that, as used in the specification and the appended claims, the singular forms "a," "an" and "the" include plural referents unless otherwise specified.

The following description discloses several preferred embodiments of magnetic storage systems, as well as operation and/or component parts thereof.

In one general embodiment, a system includes a transport mechanism for running a tape across a wear structure and a measuring device for optically measuring an extent of wear of the wear structure.

In another general embodiment, a method includes positioning a tape across a wear structure, optically determining a first position of a back of the tape relative to a measuring device using the measuring device, running the tape across the wear structure for a period of time, optically determining a second position of the back of the tape relative to the measuring device using the measuring device after the period of time, and determining a difference between the first and second positions.

In yet another general embodiment, a method for characterizing a wear stability of a material includes passing a burnished tape across a wear structure, optically determining a first position of a back of the tape relative to a measuring device using the measuring device, running the tape across the wear structure for a period of time, optically determining a second position of the back of the tape relative to the measuring device using the measuring device after the period of time, and determining a difference between the first and second positions.

Figure 1:
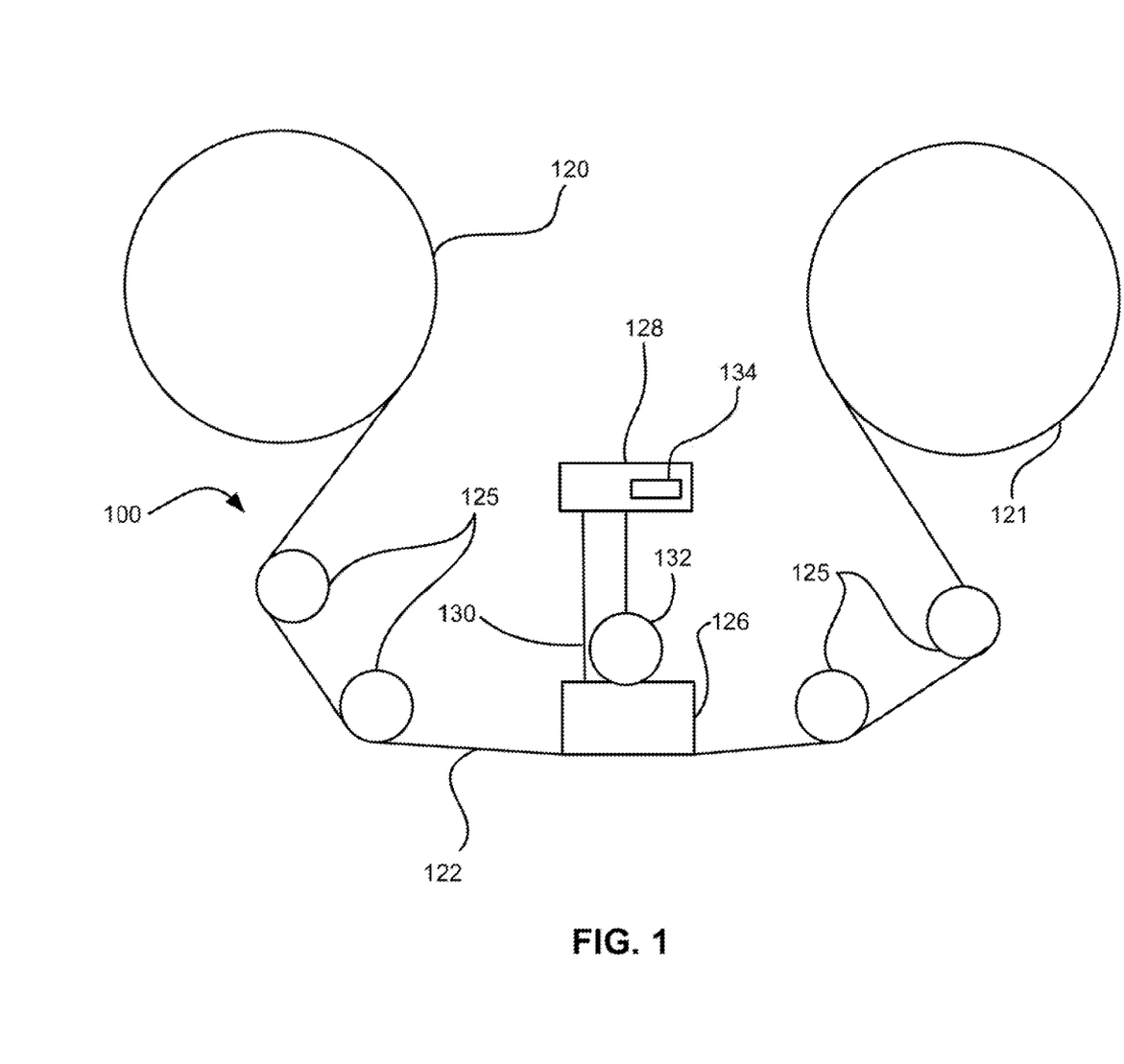
FIG. 1 is a schematic diagram of a simplified tape drive system according to one embodiment.

FIG. 1 illustrates a simplified tape drive 100 of a tape-based data storage system, which may be employed in the context of the present invention. While one specific implementation of a tape drive is shown in FIG. 1, it should be noted that the embodiments described herein may be implemented in the context of any type of tape drive system.

As shown, a tape supply cartridge 120 and a take-up reel 121 are provided to support a tape 122. One or more of the reels may form part of a removable cartridge and are not necessarily part of the system 100. The tape drive, such as that illustrated in FIG. 1, may further include drive motor(s) to drive the tape supply cartridge 120 and the take-up reel 121 to move the tape 122 over a tape head 126 of any type. Such head may include an array of readers, writers, or both.

Guides 125 guide the tape 122 across the tape head 126. Such tape head 126 is in turn coupled to a controller assembly 128 via a cable 130. The controller 128 typically controls head functions such as servo following, writing, reading, etc. The controller may operate under logic known in the art, as well as any logic disclosed herein. The cable 130 may include read/write circuits to transmit data to the head 126 to be recorded on the tape 122 and to receive data read by the head 126 from the tape 122. An actuator 132 controls position of the head 126 relative to the tape 122.

An interface 134 may also be provided for communication between the tape drive and a host (integral or external) to send and receive the data and for controlling the operation of the tape drive and communicating the status of the tape drive to the host, all as will be understood by those of skill in the art.

Figure 2:
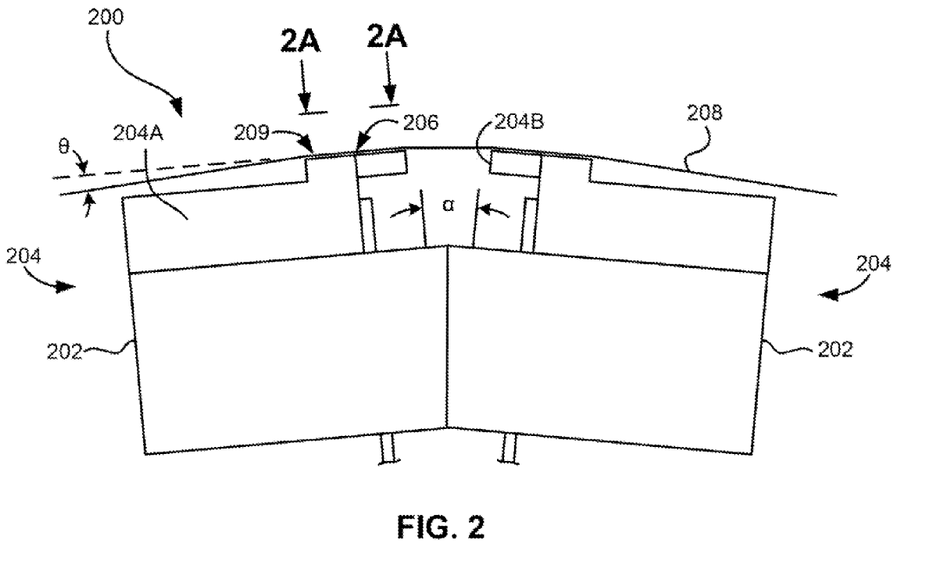
FIG. 2 illustrates a side view of a flat-lapped, bi-directional, two-module magnetic tape head according to one embodiment.

By way of example, FIG. 2 illustrates a side view of a flat-lapped, bi-directional, two-module magnetic tape head 200 which may be implemented in the context of the present invention. As shown, the head includes a pair of modules 204, each equipped with bases 202, and fixed at a small angle α with respect to each other. The bases may be "U-beams" that are adhesively coupled together. Each module 204 includes a substrate 204A and a closure 204B with a thin film portion, commonly referred to as a "gap" in which the readers and/or writers 206 are formed. In use, a tape 208 is moved over the modules 204 along a media (tape) bearing surface 209 in the manner shown for reading and writing data on the tape 208 using the readers and writers. The wrap angle θ of the tape 208 at edges going onto and exiting the flat media support surfaces 209 are usually between about 0.1 degree and about 5 degrees.

The substrates 204A are typically constructed of a wear resistant material, such as a ceramic. The closures 204B made of the same or similar ceramic as the substrates 204A.

The readers and writers may be arranged in a piggyback or merged configuration. An illustrative piggybacked configuration comprises a (magnetically inductive) writer transducer on top of (or below) a (magnetically shielded) reader transducer (e.g., a magnetoresistive reader, etc.), wherein the poles of the writer and the shields of the reader are generally separated. An illustrative merged configuration comprises one reader shield in the same physical layer as one writer pole (hence, "merged"). The readers and writers may also be arranged in an interleaved configuration. Alternatively, each array of channels may be readers or writers only. Any of these arrays may contain one or more servo track readers for reading servo data on the medium.

Figure 2A:
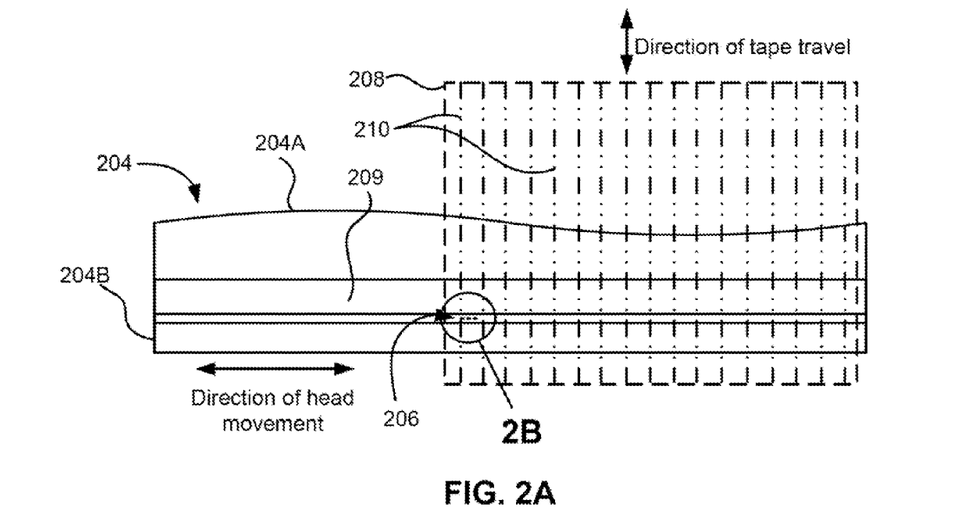
FIG. 2A is a tape bearing surface view taken from Line 2A of FIG. 2.

FIG. 2A illustrates the tape bearing surface 209 of one of the modules 204 taken from Line 2A of FIG. 2. A repre-sentative tape 208 is shown in dashed lines. The module 204 is preferably long enough to be able to support the tape as the head steps between data bands.

In this example, the tape 208 includes 4 to 22 data bands, e.g., with 16 data bands and 17 servo tracks 210, as shown in FIG. 2A on a one-half inch wide tape 208. The data bands are defined between servo tracks 210. Each data band may include a number of data tracks, for example 512 data tracks (not shown). During read/write operations, the readers and/or writers 206 are positioned to specific track positions within one of the data bands. Outer readers, sometimes called servo readers, read the servo tracks 210. The servo signals are in turn used to keep the readers and/or writers 206 aligned with a particular set of tracks during the read/write operations.

Figure 2B:
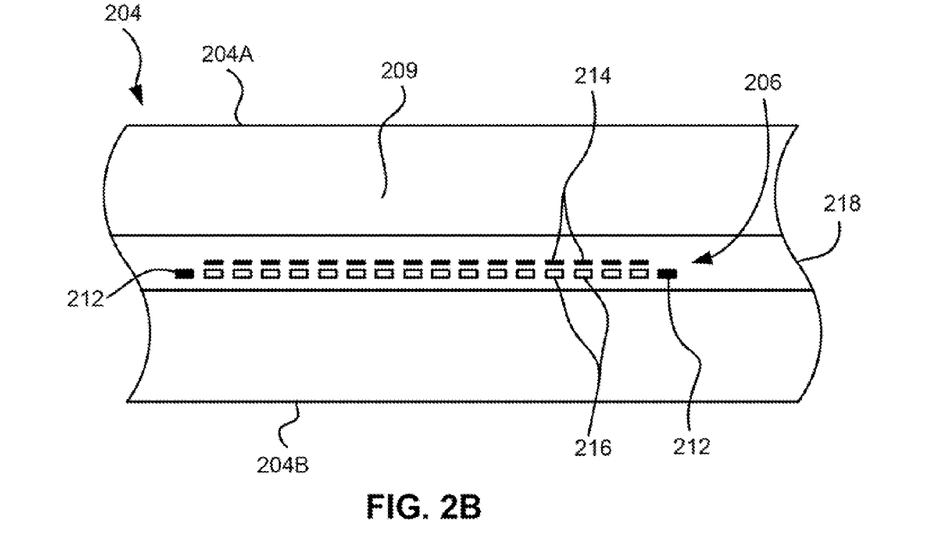
FIG. 2B is a detailed view taken from Circle 2B of FIG. 2A.

FIG. 2B depicts a plurality of readers and/or writers 206 formed in a gap 218 on the module 204 in Circle 2B of FIG. 2A. As shown, the array of readers and writers 206 includes, for example, 16 writers 214, 16 readers 216 and two servo readers 212, though the number of elements may vary. Illustrative embodiments include 8, 16, 32, 40, and 64 readers and/or writers 206 per array. A preferred embodiment includes 32 readers per array and/or 32 writers per array, where the actual number of transducing elements could be greater, e.g., 33, 34, etc. This allows the tape to travel more slowly, thereby reducing speed-induced tracking and mechanical difficulties and/or execute fewer "wraps" to fill or read the tape. While the readers and writers may be arranged in a piggyback configuration as shown in FIG. 2B, the readers 216 and writers 214 may also be arranged in an interleaved configuration. Alternatively, each array of readers and/or writers 206 may be readers or writers only, and the arrays may contain one or more servo readers 212. As noted by considering FIGS. 2 and 2A-B together, each module 204 may include a complementary set of readers and/or writers 206 for such things as bi-directional reading and writing, read-while-write capability, backward compatibility, etc.

Figure 2C:
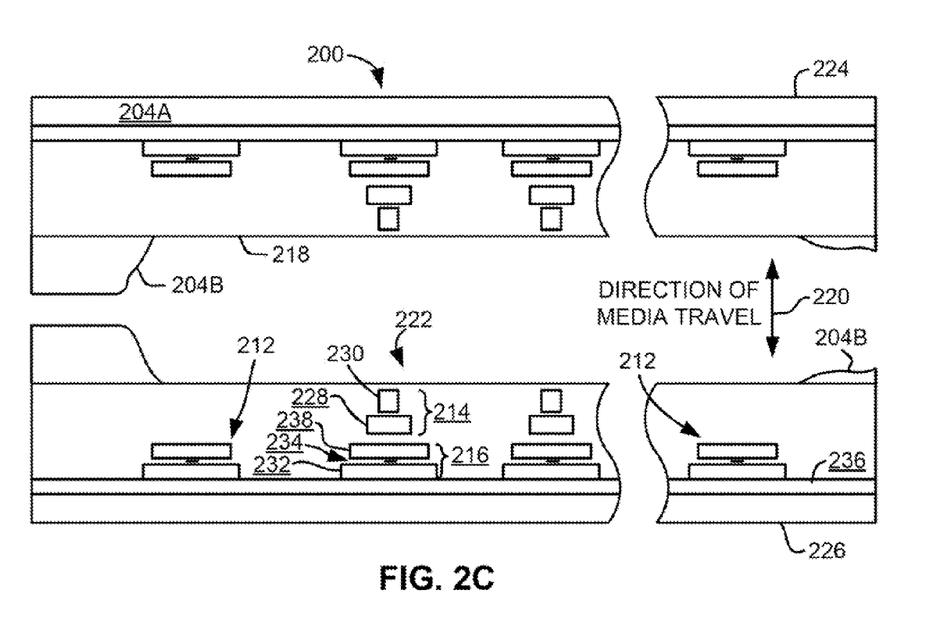
FIG. 2C is a detailed view of a partial tape bearing surface of a pair of modules.

FIG. 2C shows a partial tape bearing surface view of complimentary modules of a magnetic tape head 200 according to one embodiment. In this embodiment, each module has a plurality of read/write (R/W) pairs in a piggyback configuration formed on a common substrate 204A and an optional electrically insulative layer 236. The writers, exemplified by the write head 214 and the readers, exemplified by the read head 216, are aligned parallel to a direction of travel of a tape medium thereacross to form an R/W pair, exemplified by the R/W pair 222.

Several R/W pairs 222 may be present, such as 8, 16, 32 pairs, etc. The R/W pairs 222 as shown are linearly aligned in a direction generally perpendicular to a direction of tape travel thereacross. However, the pairs may also be aligned diagonally, etc. Servo readers 212 are positioned on the outside of the array of R/W pairs, the function of which is well known.

Generally, the magnetic tape medium moves in either a forward or reverse direction as indicated by arrow 220. The magnetic tape medium and head assembly 200 operate in a transducing relationship in the manner well-known in the art. The piggybacked MR head assembly 200 includes two thin-film modules 224 and 226 of generally identical construction.

Modules 224 and 226 are joined together with a space present between closures 204B thereof (partially shown) to form a single physical unit to provide read-while-write capability by activating the writer of the leading module and reader of the trailing module aligned with the writer of the leading module parallel to the direction of tape travel relative thereto. When a module 224, 226 of a piggyback head 200 is constructed, layers are formed in the gap 218 created above an electrically conductive substrate 204A (partially shown), e.g., of AlTiC, in generally the following order for the R/W pairs 222: an insulating layer 236, a first shield 232 typically of an iron alloy such as NiFe (permalloy), CZT or Al—Fe—Si (Sendust), a sensor 234 for sensing a data track on a magnetic medium, a second shield 238 typically of a nickel-iron alloy (e.g., 80/20 Permalloy), first and second writer pole tips 228, 230, and a coil (not shown).

The first and second writer poles 228, 230 may be fabricated from high magnetic moment materials such as 45/55 NiFe. Note that these materials are provided by way of example only, and other materials may be used. Additional layers such as insulation between the shields and/or pole tips and an insulation layer surrounding the sensor may be present. Illustrative materials for the insulation include alumina and other oxides, insulative polymers, etc.

Each drive product has different generations and each generation typically results in creation of a newly formulated tape that is usually smoother, less abrasive and has denser magnetic particle packing than the previous generation.

The current method employed by media vendors to gauge tape abrasivity involves running tape over the tip of a triangular shaped AlFeSil wear structure. This method has been shown to not be representative of actual head wear, and not a good gauge of tape abrasivity.

According to a preferred embodiment, a testing system and/or methodology may be used for gauging media abrasivity relative to particular types of modules. Various embodiments disclosed herein more accurately measure media abrasivity and/or are more representative of the head wear observed in actual product usage, in addition to being fast, accurate, and easy to use.

Figure 3:
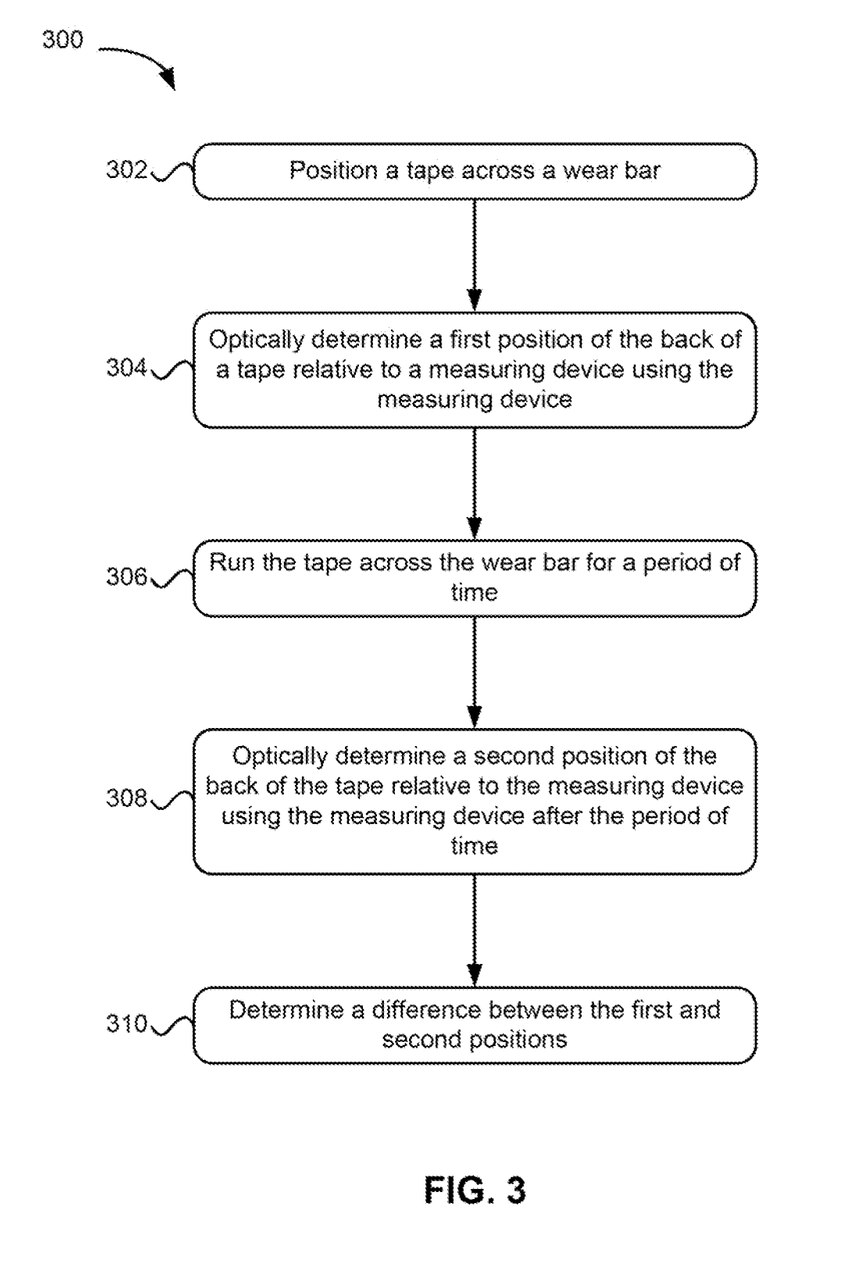
FIG. 3 depicts a method according to one embodiment.

FIG. 3 depicts a method 300 for characterizing an abrasivity of a tape and/or characterizing a wear characteristic of a material or materials, in accordance with one embodiment. As an option, the present method 300 may be implemented in conjunction with features from any other embodiment listed herein, such as those described with reference to the other FIGS, such as FIGS. 4-6B. Of course, however, such method 300 and others presented herein may be used in various applications and/or in permutations which may or may not be specifically described in the illustrative embodiments listed herein. Further, the method 300 presented herein may be used in any desired environment. Thus FIG. 3 (and the other FIGS.) should be deemed to include any and all possible permutations.

Now referring to FIG. 3, the method 300 includes positioning a tape across a wear structure. See operation 302. In various embodiments, the tape passed across a wear structure may be burnished, damaged, green (e.g., unused), etc. With reference to the present description, a "burnished" tape is a tape that has had the relevant (burnished) area of the tape passed across a copy of the substrate to be tested at least twice. However, the burnished tape may have alternatively been passed across a magnetic head, other type of wear structure, etc., in other embodiments. The passes tend to remove a significant portion of abrasive asperities from the tape, and thus a green (e.g., unused) tape is generally more abrasive than a tape that has experienced wear.

According to various embodiments, the tape may include a newly formulated tape, a tape from a previous generation, a tape selected from a bank of tapes, etc.

As illustrated in operation 304, the method 300 also includes optically determining a first position of a back of the tape (i.e., the side of the tape not facing the wear structure) relative to a measuring device (or equivalently any other stationary reference point, object or surface in the system) using the measuring device. Further illustrated in method 300, operation 306 includes running the tape across the wear structure for a period of time. According to different embodiments, the period of time may be some periodic interval, a randomly and/or user selected time period, etc.

With continued reference to FIG. 3, the method includes optically determining a second position of the back of the tape relative to the measuring device using the measuring device after the period of time. See operation 308. As mentioned above, the back of the tape is intended to include the side of the tape not facing the wear structure, e.g., as shown in FIGS. 4-6B.

Furthermore, operation 310 includes determining a difference between the first and second positions. It follows that the difference between the first and second positions may be indicative of an amount of wear of the wear structure caused by the running tape.

According to preferred embodiments, a first and/or second position may be optically determined while the tape is moving across the wear structure. However in other embodiments, the optical determination may be made when the tape is stationary. Moreover, measurements may be made before a tape is positioned above the wear structure and/or after the tape is removed from the wear structure. Illustrative devices for performing the measuring are described below.

Note that operations 304-310 may be repeated, e.g., to determine a rate of wear over multiple time periods. Moreover, measurements to determine positions of the back of the tape can be taken continuously in some embodiments.

Figure 4:
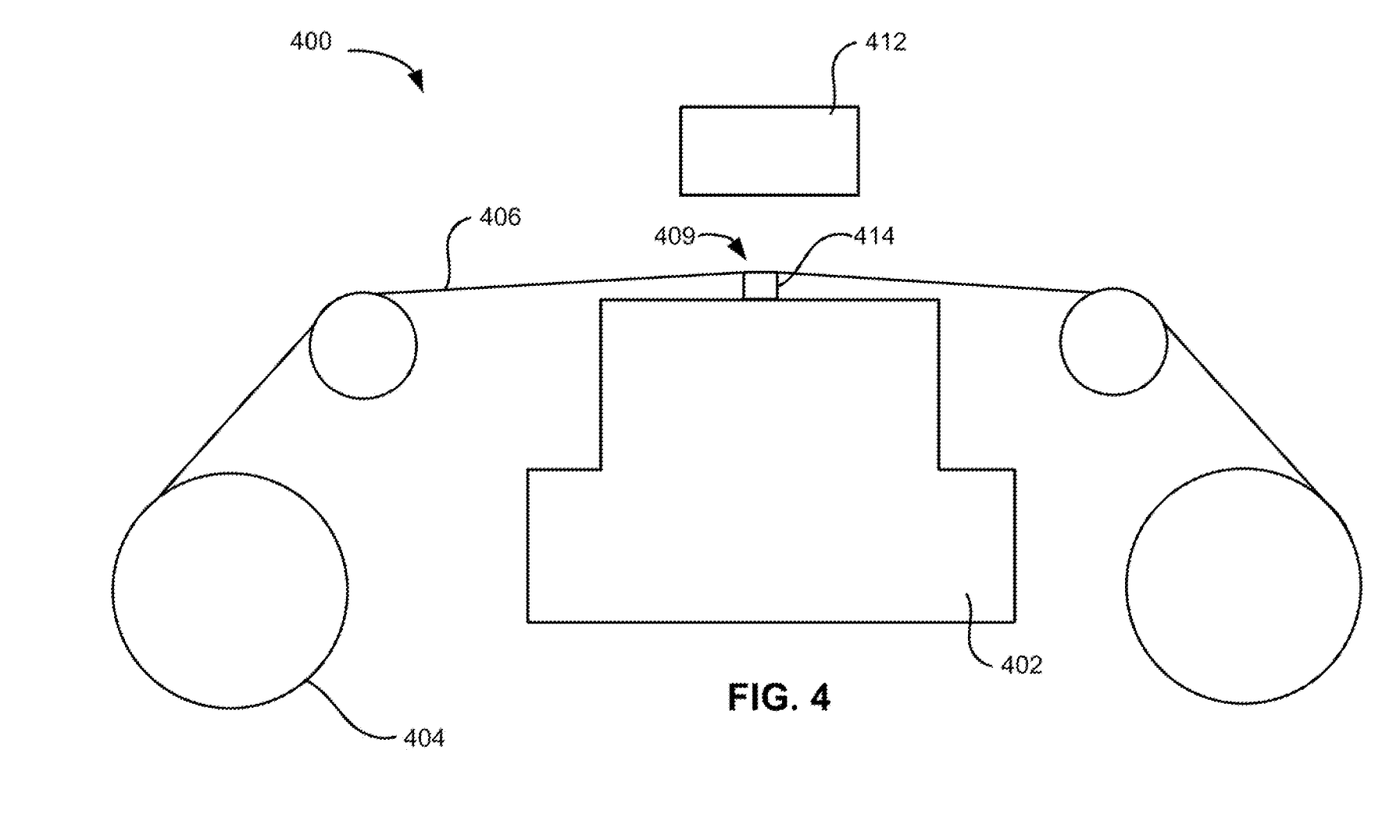
FIG. 4 is a partial cross-sectional view of a system according to one embodiment.

FIG. 4 depicts a system 400, in accordance with one embodiment. As an option, the present system 400 may be implemented in conjunction with features from any other embodiment listed herein, such as those described with reference to the other FIGS, such as the method 300 of FIG. 3. Of course, however, such system 400 and others presented herein may be used in various applications and/or in permutations which may or may not be specifically described in the illustrative embodiments listed herein. Further, the system 400 presented herein may be used in any desired environment. Thus FIG. 4 (and the other FIGS.) should be deemed to include any and all possible permutations.

Referring now to FIG. 4, the system 400 includes a carrier 402 which may be configured to receive a wear structure 414. In various embodiments, the carrier 402 may include plastic, glass, ceramic, metal, etc., or any other material which would be apparent to one skilled in the art upon reading the present description. Moreover, the carrier 402 may include a coupling mechanism (not shown) such as a slot, clamp, etc. for coupling the wear structure 414 to the carrier 402.

The system 400 additionally includes a transport mechanism 404 for running a tape 406 across the tape bearing surface 409 of the wear structure 414, preferably to test the wear characteristics of the wear structure 414, as will be described in further detail below. The wear structure 414 may be any functional structure that is in production, may go into production, or simply has a shape similar to a structure that may or will be used in a product.

According to some embodiments, the wear structure 414 may be an actual magnetic head. However, in other embodiments, the wear structure 414 may be nonfunctional, as in a case where the wear structure 414 may be a dummy module, a replica, a defective real module, etc. Thus, a wear structure 414 may look like a tape head (e.g., see 126 of FIG. 1), have a similar composition, etc. and may or may not have transducing elements. Such nonfunctional embodiments may be used to reduce the production time and cost of the testing platform.

In a preferred embodiment, the wear structure 414 may be at least about 10 nanometers thick, more preferably from about 50 nanometers to about 200 nanometers, but may be higher or lower in various embodiments. An illustrative width in the direction of tape travel may be approximately comparable to a width of the tape tents formed at the corners of the tape bearing surface. After the tape runs for a while, the coating evolves into a stable cylindrical contour, at which point an additional tape contact pressure term is T/RW, where T is tape tension, R is the radius of the contour, and W is the width of the tape. Dimensions for the wear structure 414 within the aforementioned range are desirable for evaluating wear resistance of head materials, as well as thicker and/or harder coatings.

Dummy modules may be constructed of a single material including permalloy, alumina, AlTiC, etc., or any other material. It should be noted that for embodiments which include alumina in the wear structure 414, it is preferable that the alumina be deposited in a manner such that it grows in a crystalline, polycrystalline, or semi-crystalline fashion thereby preventing the tape 406 from wearing down the wear structure 414 too quickly. In a particularly preferred embodiment, the wear structure 414 may primarily e.g., at least 50% up to 100%, polycrystalline alumina.

In other embodiments, some of which are described below, the wear structure 414 may be constructed of multiple materials, laminates, etc. For example, the wear structure 414 may have a coating layer above a substrate, where the coating layer is the wear surface of interest.

Furthermore, for wear measurements to be accurate and meaningful, a wear structure with an appropriate hardness may preferably be selected such that the difference in tape abrasivity can be easily discerned within a relatively short period of time.

In one embodiment, the wear structure may preferably have a similar coefficient of friction as a magnetic head structure of interest, e.g., such that stiction and friction do not negatively affect the testing system 400.

With continued reference to FIG. 4, the system 400 additionally includes a measuring device 412. The measuring device 412 preferably optically measures an extent of wear of the wear structure 414 on the tape bearing surface 409 as the tape 406 is run thereacross. The measuring device 412 may be configured to use areas of the tape bearing surface 409 not contacted by the tape 406, e.g., as a reference gauge while conducting measurements. In another embodiment, the carrier 402 and measuring device 412 may be configured and/or positioned to allow measuring the extent of wear of the wear structure 414 and/or its coating without removing the wear structure 414 from the carrier 402, as will be described in more detail below, with reference to FIGS. 5A-6B. Moreover, the measuring device 412 may perform part of, some of the process steps described above with reference to the method 300 of FIG. 3. In other embodiments, the extent of wear may be determined after the tape has been removed, while the tape is stationary, after the tape has been swapped with another tape, etc.

Figure 5A:
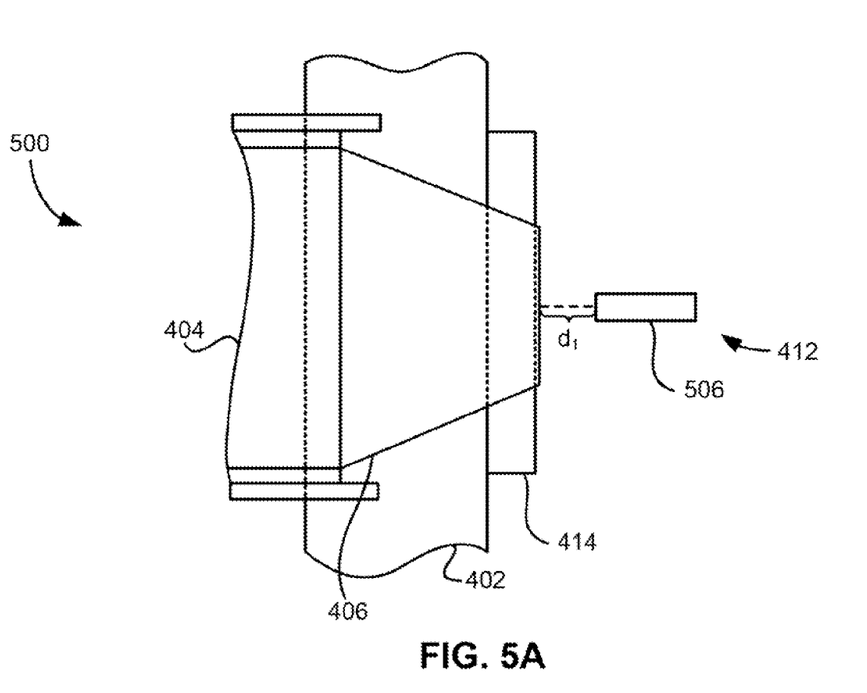
FIG. 5A is a side view of a wear and media abrasivity measuring system according to one embodiment.
Figure 5B:
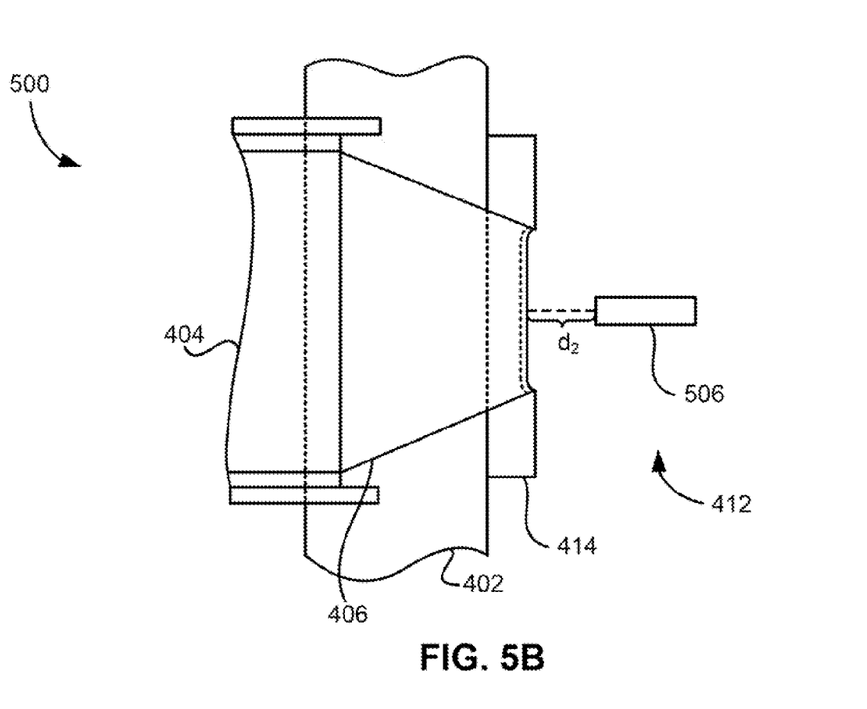
FIG. 5B is a side view of a wear and media abrasivity measuring system according to one embodiment.

FIGS. 5A-5B depict a system 500, in accordance with one embodiment. As an option, the present system 500 may be implemented in conjunction with features from any other embodiment listed herein, such as those described with reference to the other FIGS. Of course, however, such system 500 and others presented herein may be used in various applications and/or in permutations which may or may not be specifically described in the illustrative embodiments listed herein. Further, the system 500 presented herein may be used in any desired environment. Moreover, it should also be noted that FIGS. 5A-5B illustrate variations of the embodiments of FIG. 4. Accordingly, various components of FIGS. 5A-5B have common numbering with those of FIG. 4.

Looking now to FIG. 5A, once a wear structure 414 has been mounted on the carrier 402, the transport mechanism 404 may be adjusted to provide sufficient wrap of the tape 406 across the wear structure 414. In one embodiment, an initial measurement may be taken before the tape 406 is run across the wear structure 414 to define a first position $d_1$, e.g., to be used as a baseline when comparing later positions of the wear structure. According to one embodiment, this first position may correspond to a new wear installed in the system, however, in other embodiments, a first position may be established after the wear structure has been worn for some period of time. In other words, the first position may be reset at a given time and/or extent of wear, depending on the desired embodiment.

As the transport mechanism 404 operates to move the tape 406 across the wear structure 414, the wear structure 414 wears due to atmospheric pressure forcing the tape 406 against the subambient interface between the wear structure 414 and the tape 406. Thus, the friction caused by the contact between the tape 406 and the wear structure 414 gradually deteriorates the material of the wear structure 414. Additionally, the corners of the wear structure 414 serve to skive air from the tape 406 to create the aforementioned subambient condition.

As the wear structure 414 is affected by the running tape, the measuring device 412 may be used for optically measuring an extent of wear of the wear structure 414, e.g., by defining a second position $d_2$. As described above in operation 310, the difference between the first and second positions $d_1$, $d_2$ may be indicative of an amount of wear of the wear structure caused by the running tape at a given point in time.

Because the extent of wear and other parameters/configurations of the system and wear structure are known, the abrasivity of the tape can be characterized using known methods, as will become apparent to one skilled in the art upon reading the present disclosure.

According to various embodiments, the wear structure 414 and measuring device 412 may be configured and/or positioned to allow measuring the extent of wear of the wear structure 414 while the tape 406 engages the wear structure 414. In some embodiments, the tape 406 may be still during any of the measurements, while in other embodiments, the tape 406 may be running across the wear structure 414. Thus, in some embodiments, the wear structure 414 and measuring device 412 may be configured and/or positioned to allow measuring the extent of wear of the wear structure 414 while the tape 406 is running thereacross. However, in other embodiments, measurements for determining the extent of wear may be made before a tape 406 is positioned above the wear structure 414 and/or after the tape 406 is removed from the wear structure 414.

It follows that the wear structure 414 and measuring device 412 may be configured and/or positioned to allow measuring the extent of wear of the wear structure 414 without removing the wear structure 414 from the carrier 402. According to a preferred embodiment, the measuring device 412 may include a spectral interference meter 506. Illustrative spectral interference meters include the SI-F series Micro-Head Spectral-Interference Laser Displacement Meter sold by Keyence Corporation of America, 1100 North Arlington Heights Road, Suite 210, Itasca, Ill. 60143.

However, in other embodiments, the wear of the wear structure 414 may be measured using any of the measuring devices mentioned and/or suggested herein.

An extent of wear of the wear structure 414 may be measured at regular and/or nonregular intervals, continuously, etc. For example, the tape 406 may be run across the wear structure 414 for a short period, and then a wear measurement may be taken using the spectral interference meter 506, followed by running the tape 406 again for a second period and re-measuring, and so on.

It is preferable that residual thickness is measured near the center of the coating as measured in a direction of tape travel, as the coating near the corners of the wear structure may exhibit a wear pattern resulting from tape tenting, and thus would give inaccurate readings if used as the residual thickness. Looking to FIG. 5B, the wear of the wear structure 414 may be about uniform across the tape bearing side of a wear structure having a single material composition, e.g., such that the residual thickness measurement made by the spectral interference meter 506 at one location is an accurate reading for a majority of the extent of wear of the wear structure 414. However, depending on the material composition and/or dimensions of the wear structure, different portions of the wear structure may wear faster or slower than other portions. Accordingly, the measuring device may include more than one spectral interference meter 506, as will soon become apparent.

Figure 6A:
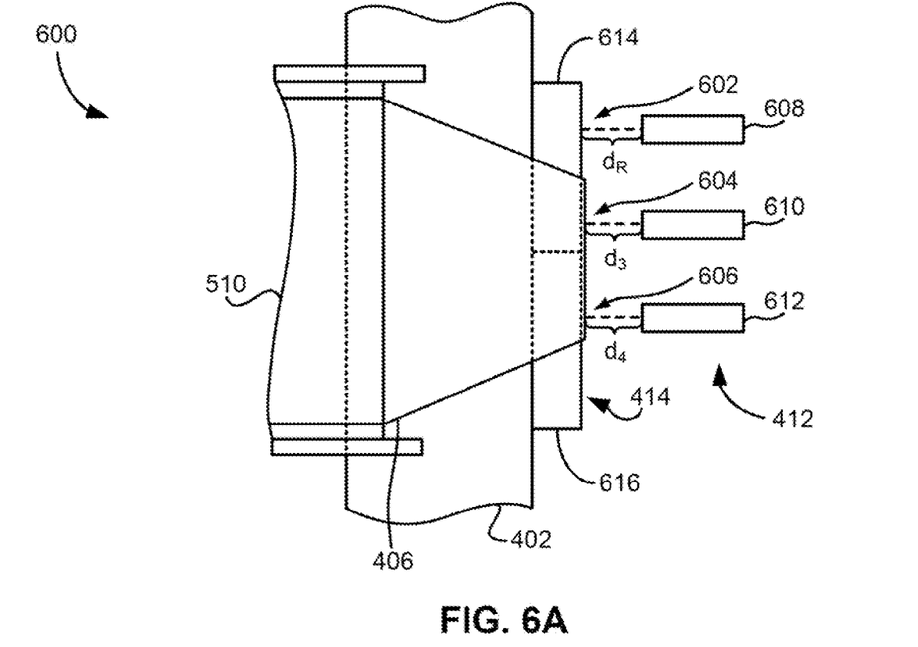
FIG. 6A is a side view of a wear and media abrasivity measuring system according to one embodiment.
Figure 6B:
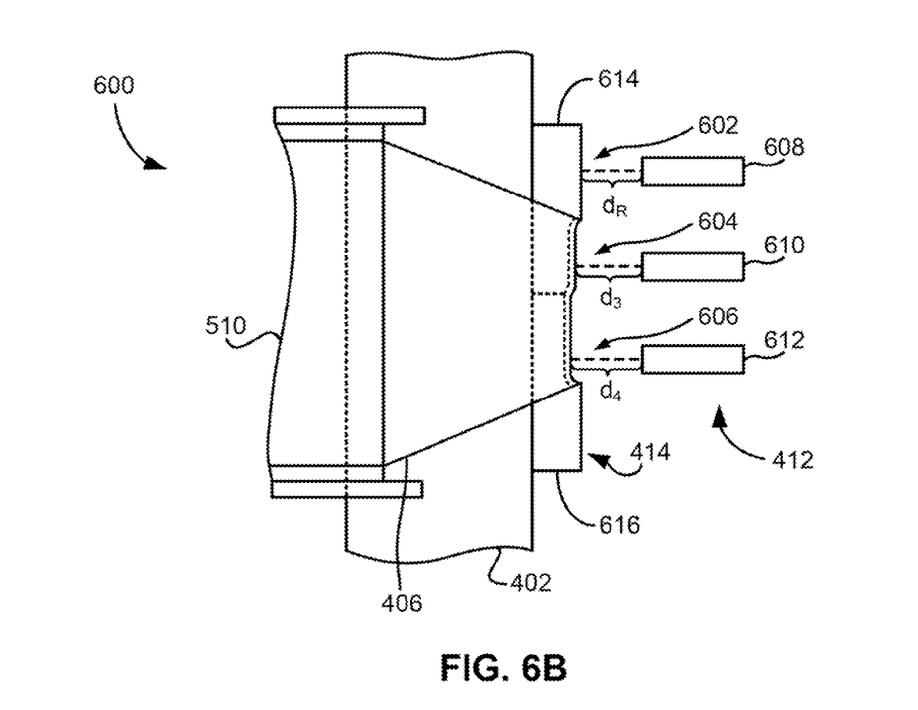
FIG. 6B is a side view of a wear and media abrasivity measuring system according to one embodiment.

FIGS. 6A-6B depict a system 600, in accordance with one embodiment. As an option, the present system 600 may be implemented in conjunction with features from any other embodiment listed herein, such as those described with reference to the other FIGS. Of course, however, such system 600 and others presented herein may be used in various applications and/or in permutations which may or may not be specifically described in the illustrative embodiments listed herein. Further, the system 600 presented herein may be used in any desired environment. Moreover, it should also be noted that FIGS. 6A-6B illustrate variations of the embodiments of FIGS. 5A-5B. Accordingly, various components of FIGS. 6A-6B have common numbering with those of FIGS. FIGS. 5A-5B.

Referring now to FIGS. 6A-6B, the system 600 includes a measuring device 412 which has multiple spectral interference meters 608, 610, 612. It is preferred, but not required, that each of the spectral interference meters 608, 610, 612 is calibrated such that they have substantially the same accuracy when making measurements. However, in other embodiments, differences in tolerances of the spectral interference meters 608, 610, 612 may be compensated for using computing (e.g., offsets).

According to the illustrated embodiment, the measuring device 412 may be configured to measure wear at two or more different locations 602, 604, 606 along a portion of a wear structure 414 contacted by the tape 406. According to one embodiment, the different locations 602, 604, 606 may correspond to sections 614, 616 of the wear structure 414 constructed of different materials. e.g., having different wear characteristics. Such testing configurations may be especially useful when different portions of a wear structure 414 include different soft materials which may not require a long period of running the tape 406 before notable non-uniform wear becomes present. According to various embodiments, the materials used to form the different sections 614, 616 of the wear structure 414 may include any of the wear materials described and/or suggested herein.

Accordingly, in a preferred embodiment, the spectral interference meters 608, 610, 612 may be configured and/or positioned to allow measuring the non-uniform extent of wear $d_3$, $d_4$ of the wear structure 414 while the tape 406 is running thereacross. Thus, embodiments such as the one illustrated in FIGS. 6A-6B may create a platform that allows for the simultaneous testing of multiple wear materials, thereby increasing overall efficiency.

As illustrated in FIGS. 6A-6B, one of the spectral interference meters 608 of the measuring device 412 may correspond to an area of the wear structure 414 not contacted by the tape 406 to define a first position $d_R$, e.g., to be used as a baseline when comparing later positions of the wear structure. Thus, as the tape 406 runs over the wear structure 414 during testing, the first position $d_R$ may be used to determine the extent of wear at the other locations 604, 606 along the wear structure 414 affected by the tape 406. In an alternate embodiment, noted above, the initial position of the wear structure 414 may be measured prior to running the tape.

As mentioned above, the extent of wear at a given location may be determined by the difference between the first position $d_R$ and a second and/or third position $d_2$, $d_3$. Thus, the extent of wear measured may be accurately indicative of an amount of wear of the wear structure caused by the running tape at a given point in time. It follows that the second and/or third positions are determined above each of the respective portions 614, 616 of the wear structure 414, above the tape 406 positioned thereabove.

It may be desirable to record the first, second and third positions $d_R$, $d_3$, $d_4$ at about the same time during testing, e.g., such that any environmental conditions, e.g., vibrations, temperatures, contaminants, etc. affects both the test and reference measurements equally. Therefore, by subtracting the two measurements to achieve the extent of wear, the environmental conditions are canceled from the data in the calculated results.

Figure 7:
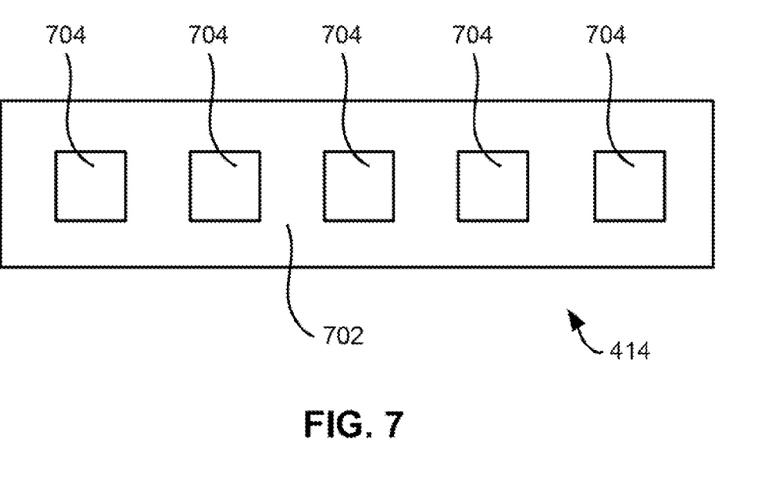
FIG. 7 is a top-down view of a wear structure scheme according to one embodiment.

Looking to the top down view of an exemplary wear structure 414 depicted in FIG. 7, according to an illustrative embodiment, the wear structure 414 may include a bulk material 702 and one or more sections of a second material 704 at predetermined positions relative to the bulk material 702. Preferably, the bulk and second materials are different, e.g., do not consist of the same material(s). In one embodiment, the second material 704 may include aluminum-iron-silicon (AlFeSil), Sendust, etc. In another embodiment, the bulk material 702 may include, but is not limited to alumina or any other suitable material described or alluded to herein. The sections of the second material may have any shape, and may be arranged in any manner. The design depicted in FIG. 7 allows for the possibility of differential wear which may allow for different sections of the coating to wear down at different rates as described above with reference to FIGS. 6A-6B. Moreover, this differential wear may provide additional information as to the wear rates of different materials applied in different testing schemes.

In further embodiments, the testing system may be operated with opposing modules, single modules, triple modules, etc.

Depending on the abrasivity of the tape media, the wear structure may wear at different rates. According to the embodiments described herein, measurements of the extent of wear of the wear structure having a shape like a tape head of interest reveal how quickly a certain tape media may be wearing the material of the wear structure. These measurements are directly related to media abrasivity and how quickly the media will wear a given module of interest while subjected to actual product usage.

According to one embodiment, the wear test, according to any of the embodiments described herein, may be conducted on any newly developed material, e.g., to compare the characteristics of the material with some standard or threshold of tape head wear to evaluate the particular material's configuration.

Additionally, optical and/or stylus profile measurements may be taken at the end of the test to capture the overall head profile created by the tape.

It will be clear that the various features of the foregoing methodologies may be combined in any way, creating a plurality of combinations from the descriptions presented above.

It will also be clear to one skilled in the art that the methodology of the present invention may suitably be embodied in a logic apparatus comprising logic to perform various steps of the methodology presented herein, and that such logic may comprise hardware components or firmware components.

It will be equally clear to one skilled in the art that the logic arrangement in various embodiments may suitably be embodied in a logic apparatus comprising logic to perform various steps of the method, and that such logic may comprise components such as logic gates in, for example, a programmable logic array. Such a logic arrangement may further be embodied in enabling means or components for temporarily or permanently establishing logical structures in such an array using, for example, a virtual hardware descriptor language, which may be stored using fixed or transmittable carrier media.

It will be appreciated that the methodology described above may also suitably be carried out fully or partially in software running on one or more processors (not shown), and that the software may be provided as a computer program element carried on any suitable data carrier (also not shown) such as a magnetic or optical computer disc. The channels for the transmission of data likewise may include storage media of all descriptions as well as signal carrying media, such as wired or wireless signal media.

Embodiments of the present invention may suitably be embodied as a computer program product for use with a computer system. Such an implementation may comprise a series of computer readable instructions either fixed on a tangible medium, such as a computer readable medium, for example, diskette, CD-ROM, ROM, or hard disk, or transmittable to a computer system, via a modem or other interface device, over either a tangible medium, including but not limited to optical or analogue communications lines, or intangibly using wireless techniques, including but not limited to microwave, infrared or other transmission techniques. The series of computer readable instructions embodies all or part of the functionality previously described herein.

Those skilled in the art will appreciate that such computer readable instructions can be written in a number of programming languages for use with many computer architectures or operating systems. Further, such instructions may be stored using any memory technology, present or future, including but not limited to, semiconductor, magnetic, or optical, or transmitted using any communications technology, present or future, including but not limited to optical, infrared, or microwave. It is contemplated that such a computer program product may be distributed as a removable medium with accompanying printed or electronic documentation, for example, shrink-wrapped software, preloaded with a computer system, for example, on a system ROM or fixed disk, or distributed from a server or electronic bulletin board over a network, for example, the Internet or World Wide Web.

Communications components such as input/output or I/O devices (including but not limited to keyboards, displays, pointing devices, etc.) can be coupled to the system either directly or through intervening I/O controllers.

Communications components such as buses, interfaces, network adapters, etc. may also be coupled to the system to enable the data processing system, e.g., host, to become coupled to other data processing systems or remote printers or storage devices through intervening private or public networks. Modems, cable modem and Ethernet cards are just a few of the currently available types of network adapters.

It will be further appreciated that embodiments of the present invention may be provided in the form of a service deployed on behalf of a customer to offer service on demand.

While various embodiments have been described above, it should be understood that they have been presented by way of example only, and not limitation. Thus, the breadth and scope of an embodiment of the present invention should not be limited by any of the above-described exemplary embodiments, but should be defined only in accordance with the following claims and their equivalents.

What is claimed is:

1. A system, comprising:
  a transport mechanism for running a tape across an initially-flat surface of a wear structure; and
  a measuring device for optically measuring an extent of wear of the initially-flat surface of the wear structure by directly optically detecting a back of the tape.

2. A system as recited in claim 1, wherein the wear structure has a skiving edge for skiving air from the tape to create a subambient interface between the wear structure and the tape along the initially-flat surface.

3. A system as recited in claim 1, wherein the wear structure and measuring device are configured and/or positioned to allow measuring the extent of wear of the wear structure while the tape engages the wear structure.

4. A system as recited in claim 3, wherein the wear structure and measuring device are configured and/or positioned to allow measuring the extent of wear of the wear structure while the tape is running thereacross.

5. A system as recited in claim 1, wherein the measuring device includes a spectral interference meter that acquires optical measurements by optically detecting a back of the tape.

6. A system as recited in claim 1, wherein the measuring device is configured to use an area of the wear structure not contacted by the tape as a reference gauge for the measuring.

7. A system as recited in claim 1, wherein the measuring device is configured to simultaneously measure wear at two different locations along a portion of the wear structure contacted by the tape by optically detecting two positions along the back of the tape.

8. A method, comprising:
  positioning a tape across a wear structure, the wear structure having a skiving edge for skiving air from the tape to create a subambient interface between the wear structure and the tape when the tape moves;
  optically determining a first position of a back of the tape relative to a measuring device by directly optically detecting a back of the tape using the measuring device;

running the tape across the wear structure for a period of time;

optically determining a second position of the back of the tape relative to the measuring device by directly optically detecting a back of the tape using the measuring device after the period of time; and determining a difference between the first and second positions.

9. A method as recited in claim 8, wherein the first and/or second position is optically determined while the tape is moving across the wear structure, wherein the wear caused by the tape on the wear structure is due to atmospheric pressure forcing the tape against the wear structure.

10. A method as recited in claim 8, wherein the measuring device includes a spectral interference meter that acquires optical measurements by optically detecting a back of the tape.

11. A method as recited in claim 8, wherein the measuring device is configured to use an area of the wear structure not contacted by the tape as a reference gauge for the measuring.

12. A method as recited in claim 8, wherein the wear structure has multiple sections constructed of different materials along an initially-flat surface of the wear structure, the sections being simultaneously worn by the tape when the tape is run across the initially-flat surface of the wear structure.

13. A method as recited in claim 12, wherein second positions are determined for each portion of the back of the tape above one of the sections.

14. A method as recited in claim 8, wherein the tape is a green tape.

15. A method for characterizing a wear stability of a material, the method comprising:

passing a tape across an initially-flat surface of a wear structure, the wear structure having a skiving edge for skiving air from the tape to create a subambient interface between the wear structure and the tape along the initially-flat surface, wherein the wear caused by the tape on the initially-flat surface of the wear structure is due to atmospheric pressure forcing the tape toward the subambient interface between the wear structure and the tape;

optically determining a first position of a back of the tape relative to a measuring device by directly optically detecting a back of the tape using the measuring device;

running the tape across the initially-flat surface of the wear structure for a period of time;

optically determining a second position of the back of the tape relative to the measuring device by directly optically detecting a back of the tape using the measuring device after the period of time; and determining a difference between the first and second positions.

16. A method as recited in claim 15, wherein the first and/or second position is optically determined while the tape is moving across the wear structure.

17. A method as recited in claim 15, wherein the measuring device includes a spectral interference meter that acquires optical measurements by directly optically detecting the back of the tape.

18. A method as recited in claim 15, wherein the measuring device is configured to use an area of the wear structure not contacted by the tape as a reference gauge for the measuring.

19. A method as recited in claim 15, wherein the wear structure has multiple sections constructed of different materials along the initially-flat surface of the wear structure, the sections being simultaneously worn by the tape.

20. A method as recited in claim 19, wherein second positions are determined for each portion of the back of the tape above one of the sections.

* * * * *